(12) United States Patent
Leonard et al.

(10) Patent No.: US 8,283,267 B2
(45) Date of Patent: *Oct. 9, 2012

(54) FABRICS FOR THERAPEUTIC SKIN CARE BEDDING

(75) Inventors: W. Allen Leonard, Greensboro, NC (US); Neil Blanton, Chapel Hill, NC (US); Terry Montgomery, Greensboro, NC (US); Dino Montagner, San Dona di Piave (IT); Jones McCall, Greensboro, NC (US)

(73) Assignee: Precision Fabrics Group, Inc., Greensboro, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/877,495

(22) Filed: Sep. 8, 2010

(65) Prior Publication Data

US 2011/0014836 A1 Jan. 20, 2011

Related U.S. Application Data

(63) Continuation of application No. 11/152,914, filed on Jun. 13, 2005, now Pat. No. 7,816,288, which is a continuation-in-part of application No. 10/985,739, filed on Nov. 10, 2004, now abandoned.

(51) Int. Cl.
*B32B 27/12* (2006.01)
*D03D 15/00* (2006.01)

(52) U.S. Cl. .......... 442/215; 442/93; 442/121; 442/123; 442/195; 442/196; 442/208; 442/209; 442/213; 442/216

(58) Field of Classification Search .................. 442/123, 442/192, 195, 196, 208, 209, 213, 215, 216, 442/218, 220, 121; 139/420 R, 426 R
See application file for complete search history.

(56) References Cited

U.S. PATENT DOCUMENTS

| | | |
|---|---|---|
| 3,859,678 A | 1/1975 | Davis |
| 4,525,409 A | 6/1985 | Elesh |
| 4,570,268 A | 2/1986 | Freeman |
| 4,582,747 A | 4/1986 | Hirakawa et al. |
| 4,724,183 A | 2/1988 | Heiman |
| 4,726,968 A | 2/1988 | Hayashi et al. |
| 4,744,373 A | 5/1988 | Deffeves et al. |
| 4,744,374 A | 5/1988 | Deffeves et al. |
| 4,864,669 A | 9/1989 | Jones |

(Continued)

FOREIGN PATENT DOCUMENTS

JP 2005-290575 10/2005

OTHER PUBLICATIONS

"DermaSense Bed Linens Revolutionary Comfort for Sensitive Skin," National Allergy Supply, Inc.

(Continued)

*Primary Examiner* — Jenna Johnson
(74) *Attorney, Agent, or Firm* — Myers Bigel Sibley & Sajovec, P.A.

(57) ABSTRACT

A fabric for bedding which includes a woven fabric having warp yarns and filling yarns woven to provide a smooth fabric surface. One of the warp or filling yarns being at least 40% by weight of the fabric of continuous filament nylon, and the other of the warp or filling yarns being from about 0% to 60% by weight of the fabric of continuous filament polyester or nylon having non-round filament cross sections. An antimicrobial substance is topically applied or inherently available in the fabric.

34 Claims, 3 Drawing Sheets

U.S. PATENT DOCUMENTS

| | | | |
|---|---|---|---|
| 5,034,266 | A | 7/1991 | Kinlaw et al. |
| 5,190,533 | A | 3/1993 | Blackburn |
| 5,321,861 | A | 6/1994 | Dancey et al. |
| 6,277,770 | B1 | 8/2001 | Smith |
| 6,430,789 | B1 | 8/2002 | Esche et al. |
| 6,436,420 | B1 | 8/2002 | Antelman |
| 6,509,285 | B1 | 1/2003 | Yeh |
| 6,603,053 | B2 | 8/2003 | Hisanaka |
| 6,766,817 | B2 | 7/2004 | da Silva |
| 7,281,549 | B2 | 10/2007 | Metzger |
| 2001/0049883 | A1 | 12/2001 | Ryden |
| 2003/0041808 | A1 | 3/2003 | Wulforst et al. |
| 2004/0093671 | A1 | 5/2004 | Bjornberg |
| 2005/0081304 | A1 | 4/2005 | Montagner |
| 2005/0095939 | A1 | 5/2005 | Heiman |
| 2008/0279905 | A1 | 11/2008 | Kawamoto et al. |

OTHER PUBLICATIONS

DermaSilk information from http://www.alpretec.com/eng/microderma.html.

DermaTherapy Clinical Trial: Eczema & Psoriasis; 4 pages, copyright 2009.

DermaTherapy Trial: Curative & Preventative; 3 pages, copyright 2009.

DermaTherapy Trial: Hot Flashes & Night Sweats; 3 pages, copyright 2009.

http://www.webmd.com/skin-problems-and-treatments/news/20040729,"New Treatments Ease Eczema, Psoriasis," Jul. 29, 2004.

Klein, Sarah A., "Firm Touts Germ-Fighting Linens," Sep. 13, 2004, http://www.medline.com/CorporatePages/HaloShield.htm.

Lapidus et al., "Atopic dermatitis in children: Who cares? Who pays?" Journal of the American Academy, vol. 28, No. 5, Part 1, pp. 699-703, May 1993.

Lurtz et al., "Use of a Silklike Bedding Fabric in Patients with Atopic Dermatitis," Pediatric Dermatology, vol. 24, No. 4, pp. 439-443, 2008.

Reger et al., "Support Surface Interface Pressure, Microenvironment, and the Prevalence of Pressure Ulcers: an Analysis of the Literature," Ostomy Wound Management, 53(10):50-8, 2007.

International Preliminary Report on Patentability and Written Opinion of the International Searching Authority corresponding with International Application No. PCT/US2009/052285; Date of Mailing: Jan. 26, 2012; 4 pages.

FABRICS FOR THERAPEUTIC SKIN CARE BEDDING

RELATED APPLICATIONS

This application is a continuation application of U.S. patent application Ser. No. 11/152,914, filed Jun. 13, 2005, now U.S. Pat. No. 7,816,288 which is a continuation-in-part application of U.S. patent application Ser. No. 10/985,739, filed Nov. 10, 2004, now abandoned, the disclosures of which are incorporated herein by reference as if set forth in their entireties.

BACKGROUND OF THE INVENTION

The present invention relates generally to therapeutic bedding, and more specifically to bedding that includes a woven fabric having antimicrobial properties and dries quickly to aid in healing dermatitis and other skin ailments. A similar fabric for therapeutic skin care bedding is disclosed in U.S. patent application Ser. No. 10/985,739 filed Nov. 10, 2004, the entire disclosure of which is hereby incorporated by reference.

A significant portion of the world's population is afflicted with skin problems. Nearly 15 million Americans have eczema, a chronic skin condition marked by itchy, red patches of inflamed skin. Six to seven million Americans have psoriasis, which is a skin disease that causes unsightly sores and skin scales. Such skin diseases account for a large portion of annual healthcare costs. For instance, psoriasis accounts for about $3 billion dollars a year in healthcare costs. Further, the direct financial cost in the care of a child with moderate or severe eczema is substantially higher than that for the average child with asthma.

There are also non-financial costs associated with the time spent in treatment and sleep deprivation. Between two and three hours each day is generally spent treating eczema, and an average of one to two hours of sleep each night is interrupted. Indeed, skin problems impact the quality of life for both sufferers and their families.

In addition to the effects of intractable itching, skin damage, soreness, sleep loss, and the social stigma of a visible skin disease, other factors add to the burden of the disease. The standard treatments for chronic skin problems involve the routine application of antibacterial ointments to reduce the potential for infections. Other treatments include the avoidance of clothing made of irritating wool or natural fibers and the use of non-aggressive detergents on clothing and bedding. Many must also control environmental conditions to maintain the proper level of moisture on the affected skin.

Skin irritations and dermatitis are exacerbated by two factors: exposure of skin to excessive moisture, and the potential for shear force injuries caused by friction with apparel or bedding. Although other substances, such as urine, stool, perspiration or wound drainage, may contain factors other than moisture that irritate the skin, moisture alone can predispose the skin to serious injury. Friction burns on the skin frequently occur when a person moves across a coarse moist surface such as bed sheet.

Although solutions involving wearing apparel are commonly available to help alleviate skin problems, effective technologies relating to bed linens have not been readily available. There are some examples of therapeutic bedding; however they have limitations in their ability to fully address the problems associated with skin injuries. An intriguing example of skin-care apparel involves a line of products marketed under the trade name DermaSilk™. The DermaSilk technology has shown excellent clinical results in helping to heal atopic dermatitis and psoriasis, as well as skin ulcers that form as a result of diabetes. DermaSilk therapeutic apparel include undergarments and body wraps knitted of 100% silk yarns and treated with a durable antimicrobial agent.

Silk is effective in this case since silk fibers have a chemical structure very similar to that of human hair (97% protein, 3% fat, and wax matter). Silk fibers are perfectly smooth and cylindrical. As such, they do not create mechanical friction with the skin. Further, silk is naturally hygroscopic, absorbing up to 30% of its own weight in sweat without becoming wet. This is important in aiding the cure of atopic dermatitis because silk is able to maintain the moisture balance of the skin, providing a softening and soothing micro-climate next to the skin. Silk is also capable of absorbing and releasing moisture without causing irritation, because the diameter of silk's cylindrical fibers simply increase or decrease as moisture is absorbed or released. Since silk yarns are made up of tiny continuous filaments, delicate skin is not disturbed as the moisture content changes. Silk helps to reduce heavy sweating (common in children affected by atopic dermatitis), as well as minimize the loss of moisture that can aggravate skin dryness and itching. Silk is also naturally elastic. When used in a knitted construction, silk fabrics allow garments to move with the body and to remain closely bound to the skin, thereby reducing friction.

Derma Silk fabrics and apparel also incorporate a topical antimicrobial agent that provides protection to the silk fibers against a broad range of bacteria, germs, molds, and fungus. This antimicrobial treatment inhibits the survival of bacteria on the fabric and is highly effective against *Staphylococcus Aureus*, one of the major factors of worsening atopic dermatitis.

While silk has been proven effective in apparel and body wraps, there are inherent deficiencies in the use of silk fibers, yarns, and fabrics as they relate to therapeutic bed linens, such as pillowcases and sheets. Unlike knitted apparel and wraps, bed sheets and pillowcases must withstand continuous use of up to 8 to 9 hours per day, and extensive laundering and drying. Bedding is typically subjected to various chemicals and stains associated with personal hygiene. Further, bedding must withstand much greater stresses and strains associated with sleeping adults. Chloride salts in perspiration and deodorants weaken silk. Also, alcohol-based products such as hairspray and perfumes, and chemical products like nail polish remover easily damage silk fabrics. Water applied to a stain on silk can set the stain or cause a permanent stain ring. Silk cannot be presoaked in detergents or bleaches; as both will damage silk. Further, silk fabrics cannot be air-dried in the sun, since ultraviolet rays degrade silk. Therefore, silk fabrics are inappropriate for use in therapeutic bed linens.

Thus there remains a need for a non-abrasive bed linen with antimicrobial properties that may aid in the healing of skin diseases and the prevention of further skin irritation. Further, there remains a need for a cost effective bed linen that does not irritate or exacerbate a patient's dermatitis, and can withstand many washings, detergents, autoclaving, irradiation, and nightly wear as necessary.

SUMMARY OF THE INVENTION

The present invention fulfills one or more of these needs in the art by providing a fabric for bedding that involves a unique combination of polymer types and fiber configurations to form woven fabrics that are like silk in terms of aesthetics, smoothness, elongation, and moisture handling, but more durable, more stain resistant, and more suitable for bedding.

Further, the present invention also is superior to cotton-containing fabrics because the fabric dries quickly and stays smooth when wet.

The present invention is directed to a fabric for bedding which includes a woven fabric having warp yarns and filling yarns woven to provide a smooth fabric surface. In the preferred embodiment, one of the warp and filling yarns may be at least 40% by weight of the fabric of continuous filament nylon. The other of the warp and filling yarns may be from about 0% to 60% by weight of the fabric of continuous filament polyester or nylon having non-round filament cross sections. Preferably, an antimicrobial substance is topically applied or inherently available in the fabric.

Also, the warp yarns may be 100% nylon, and the filling yarns may be polyester or nylon.

The fabric is preferably woven as a twill weave or plain weave. The warp yarn may be a 40 denier, 34 filament, five twist per inch, continuous filament nylon 6-6 yarn, with the filling yarn a 75 denier, 48 filament, continuous filament textured polyester. In the most preferred embodiment, the warp yarn is a 70 denier, 48 filament, continuous filament nylon yarn, with the filling yarn a 75 denier, 36 filament, continuous filament textured polyester.

Preferably, the continuous filaments have a non-round fiber cross section, such as a star shaped cross section or a clover leaf cross section. The continuous filaments with non-round fiber cross sections typically have a cross section such that adjacent filaments form wicking channels that enhance moisture wicking and rapid drying.

Also preferably, the fabric is finished to produce a fabric with an elongation greater than about 30% per ASTM D5034-95 test for breaking strength and elongation of textile fabrics.

In the preferred embodiment, the fabric has a soil-release topical finish.

In one aspect, the present invention provides a sheet for a bed made with a woven fabric having warp yarns and filling yarns woven to provide a smooth fabric surface and sized to cover a bed. The sheet may have hems to prevent raveling of the woven fabric. Preferably, one of the warp and filling yarns is at least 40% by weight of the fabric of continuous filament nylon, and the other of the warp and filling yarns is from about 0% to 60% by weight of the fabric of continuous filament polyester or nylon having non-round filament cross sections. Preferably, an antimicrobial substance is topically applied or inherently available in the fabric.

Another aspect of the present invention is to provide a pillow case made with a woven fabric that has warp yarns and filling yarns woven to provide a smooth fabric surface. The pillow case is sewn to form a pocket to encase a pillow with an opening on one end to enable insertion of the pillow therein. One of the warp and filling yarns may be at least 40% by weight of continuous filament nylon, and the other of the warp and filling yarns may be from about 0% to 60% by weight of continuous filament polyester or nylon having non-round filament cross sections. In the preferred embodiment, an antimicrobial substance is topically applied or inherently available in the fabric.

Still another aspect of the present invention is to provide a therapeutic bedding fabric including woven fabric that has warp yarns and filling yarns woven to provide a smooth fabric surface. The warp and filling yarns are continuous and substantially free of hairiness. One of the warp and filling yarns is preferably a continuous filament yarn having a non-round filament cross section such that adjacent filaments form wicking channels. An antimicrobial substance may be topically applied or inherently available in the fabric.

An invention can also be considered as providing a method of patient therapy including covering the patient's bed with sheets having smooth surfaces even when wet; and allowing the patient to rest between the sheets. The surface roughness between the sheets and the patient's skin is reduced in comparison with the surface roughness that would exist between cotton or polyester/cotton blend fabric sheets and the patient's skin.

Desirably, the method includes the sheets having an average geometric surface roughness of 1.0 to 1.75 microns when dry as measured by the Kawabata Evaluation System FB4 Surface Tester. Preferably the sheets provide an antimicrobial efficacy against *E. Coli, Staph. Aureus, Staph. Epidermidis*, and *P. Aeruginosa* in at least one of the sheets of at least 94%. More preferably, the sheets provide an antimicrobial efficacy against *E. Coli, Staph. Epidermidis*, and *P. Aeruginosa* in at least one of the sheets of at least 99.4%

These and other aspects of the present invention will become apparent to those skilled in the art after a reading of the following description of the preferred embodiment when considered with the drawings.

DESCRIPTION OF THE PREFERRED EMBODIMENTS

A fabric for bedding is formed with a woven fabric having warp yarns and filling yarns woven to provide a smooth fabric surface. In the preferred embodiment, one of the warp or filling yarns is at least 40% by weight of the fabric of continuous filament nylon. The other of the warp or filling yarns may be from about 0% to 60% by weight of the fabric of continuous filament polyester or nylon having non-round filament cross sections.

Preferably, an antimicrobial substance is topically applied or inherently available in the fabric. In the preferred embodiment, an antimicrobial substance such as ÆGIS Microbe Shield, manufactured by ÆGIS Environments, Inc. is topically applied to the woven fabric in a standard textile finishing operation. This antimicrobial works best against the following common microbes: *Escherichia Coli, Staphylococcus Aureus, Staphylococcus Epidermidis, Pseudomonas Aeruginosa*. The antimicrobial substance may also prevent odors in the fabric.

In a preferred embodiment, the warp yarns may be 100% nylon, and the filling yarns may be polyester or nylon.

In one embodiment, the fabric is woven as a twill weave (typically a 2×1 twill) or plain weave. Yarns are woven into fabric constructions that have 80% to 100% coverage. The warp yarn may be a 40 denier, 34 filament, five twist per inch, continuous filament nylon 6-6 yarn, and the filling yarn may be a 75 denier, 48 filament, continuous filament textured polyester. In another embodiment, the warp yarn is a 70 denier, 48 filament, continuous filament, textured nylon, and the filling yarn is a 75 denier, 36 filament, continuous filament, textured polyester. Continuous filament yarns are preferred because those yarns do not have short fibers extending beyond the fabric's planar surface, thereby decreasing irritation to sensitive skin. The smooth fabric surface also accentuates this effect. In the alternative, warp yarns of about 30 denier to 100 denier, and filling yarns of about 30 denier to 100 denier may be used.

Figure 2:
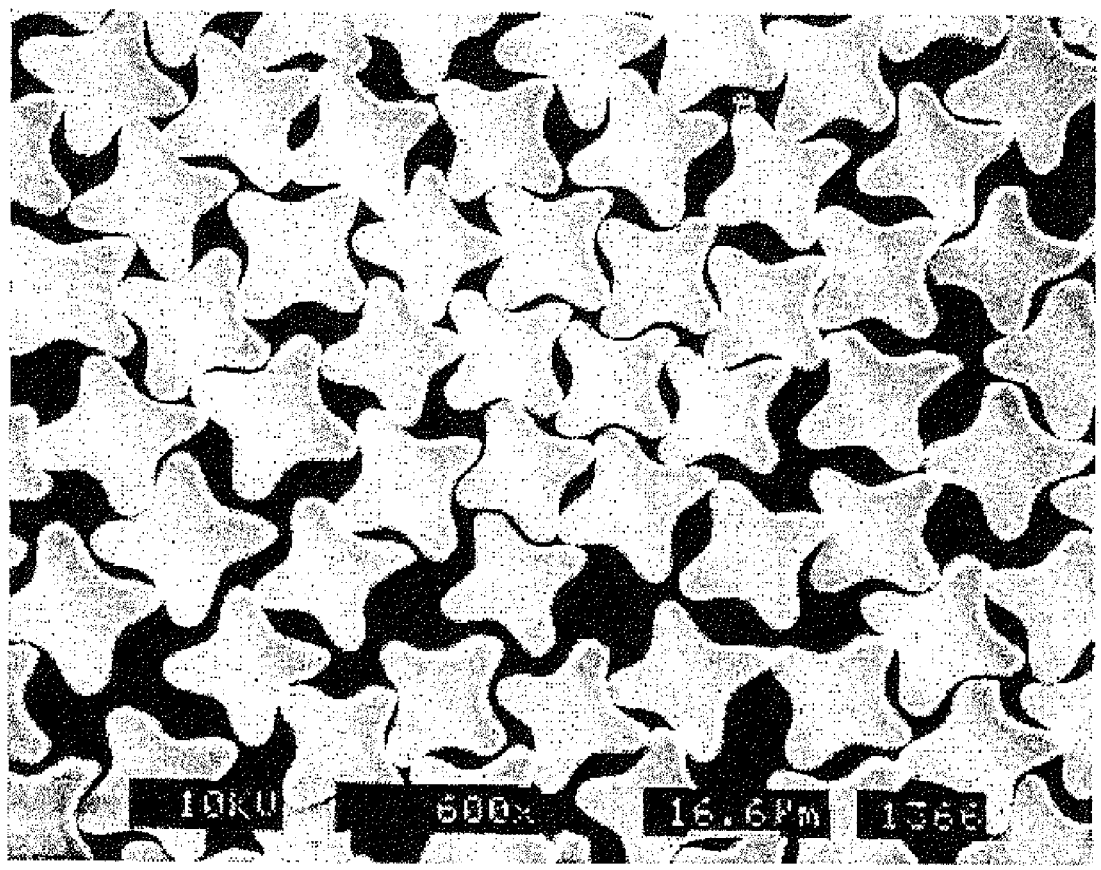
FIG. 2 is a photomicrograph of a yarn with a star-shaped fiber cross section useful in one embodiment of the invention.
Figure 3:
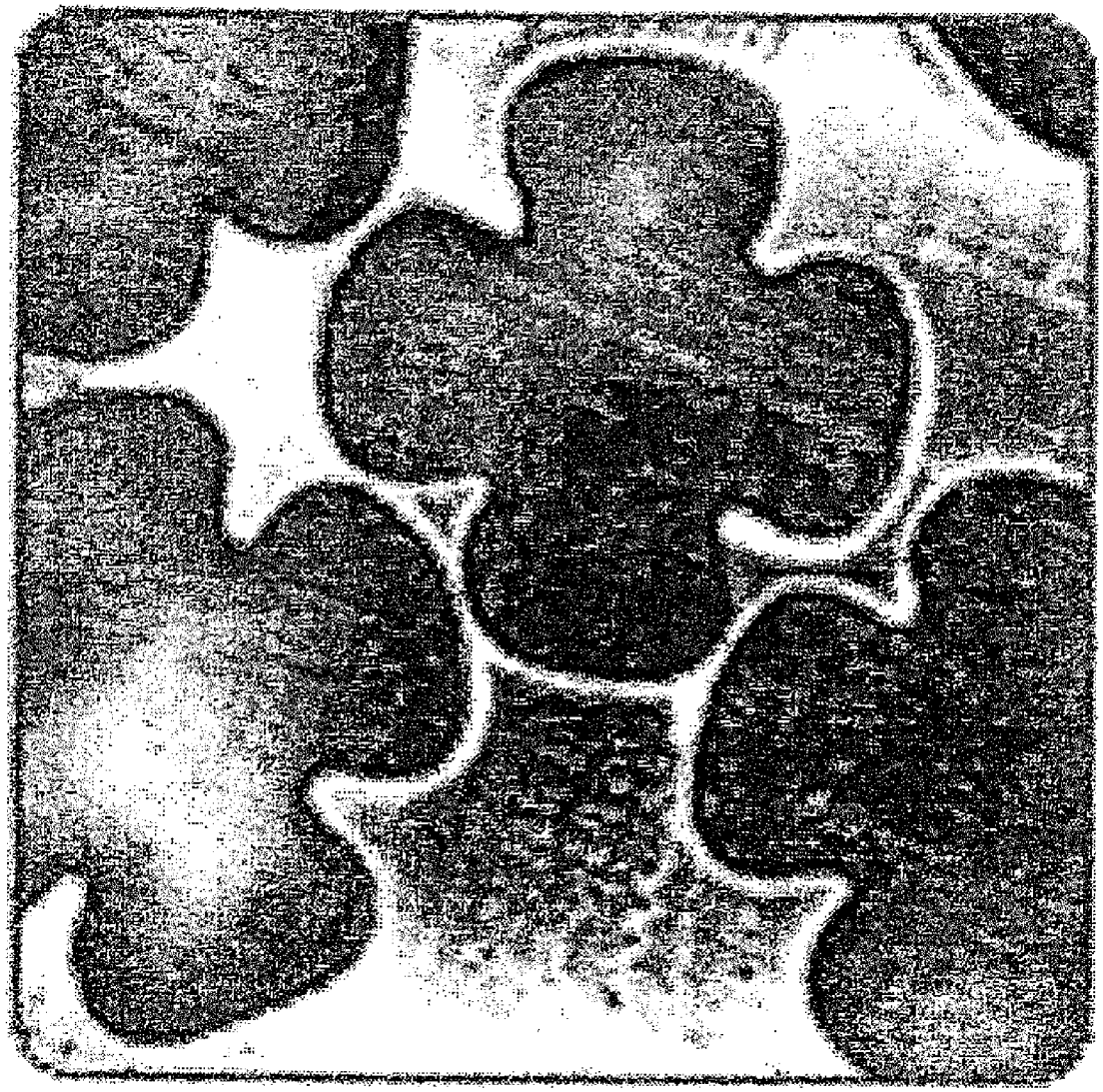
FIG. 3 is a photomicrograph of a yarn with a cloverleaf-shaped fiber cross section useful in an embodiment of the invention.

Preferably, the continuous filament has non-round fiber cross-sections such as a star shaped cross section or a clover leaf cross section. The clover-leaf cross section also improves the fabric's smoothness and softness. Examples of these are seen in FIGS. 2 and 3. With non-round fiber cross sections adjacent filaments form wicking channels along fiber surfaces to promote and enhance moisture transport away from contact with the skin. Thus, moisture more quickly evaporates and dries from the fabric surface, reducing the amount of moisture contacting the skin. As such, the wicking channels also help the user to maintain body temperature by reducing excess sweating.

In the preferred embodiment, nylon is used because it has one of the highest moisture regains of any synthetic fiber. Nylon absorbs moisture, and aids in wicking and evaporation. Although nylon is preferred, polyester can also be used if a durable auxiliary hydrophilic treatment is applied as a post finish.

In the preferred embodiment, the fabric may also contain a soil-release topical finish. Thus, the fabric is able to release stains associated with skin antibiotic creams and ointments.

Figure 1:
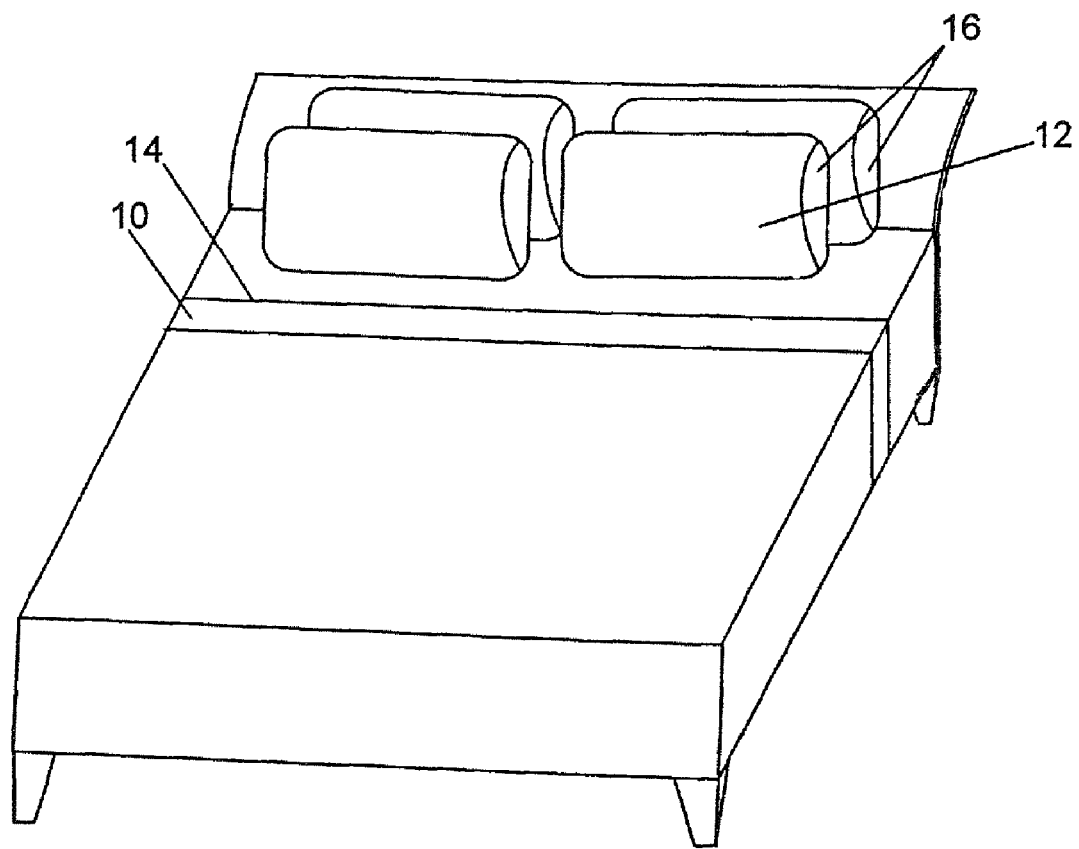
FIG. 1 is an illustration of a bed covered with a sheet and a pillow covered with a pillowcase as disclosed in the present invention.

As seen in FIG. 1, a sheet 10 for a bed is made with a woven fabric having warp yarns and filling yarns woven to provide a smooth fabric surface and sized to cover a bed. The sheet 10 may have hems 14 to prevent raveling of the woven fabric. Preferably, one of the warp or filling yarns is at least 40% by weight of the fabric of continuous filament nylon, and the other of the warp and filling yarns is from about 0% to 60% by weight of the fabric of continuous filament polyester or nylon having non-round filament cross sections. An antimicrobial substance is topically applied or inherently available in the fabric.

Also as seen in FIG. 1, a pillowcase 12 is made with a woven fabric as described above. The pillowcase 12 is sewn to form a pocket to encase a pillow with an opening 16 on one end to enable insertion of the pillow therein. One of the warp or filling yarns is at least 40% by weight of the fabric of continuous filament nylon, and the other of the warp or filling yarns is from about 0% to 60% by weight of the fabric of continuous filament polyester or nylon having non-round filament cross sections. In the preferred embodiment, an antimicrobial substance is topically applied or inherently available in the fabric.

Preferred fabrics have the following properties:

High moisture regain. Nylon, with one of the highest moisture regains of any synthetic fiber, absorbs moisture and aids in wicking and evaporation.

Excellent moisture transport. Non-round fiber cross sections create channels along fiber surfaces to promote and enhance moisture transport away from contact with the skin. Moisture more quickly evaporates and dries, and thereby reduces the amount of wetness next to the skin. As such, it helps the user to maintain body temperature by reducing excess sweating. Preferably, the fabric is 100% dry after 1 hour.

Minimal friction with the skin. Continuous-filament yarns have no short fibers extending beyond the fabric's planar surface to irritate sensitive skin. A smooth fabric surface accentuates this effect. Preferably, the fabric has an average geometric roughness of less than about 1.7 microns as measured by the Kawabata Evaluation System FB4 Surface Tester.

A good degree of stretch and recovery. Such fabrics help bed sheets to fit tighter and thereby reduce wrinkling that causes skin irritation. Such fabrics also better conform to the body and reduce the shear forces on sensitive skin. Preferably, the fabric is finished to produce a fabric with an elongation greater than about 30% as measured by ASTM D5034-95.

Durability to extended laundering and drying. Such fabrics will not loose fibers during laundering (in comparison with cotton blends), and are not afflicted with fiber pills that further irritate skin.

Able to withstand high wash temperatures and the use of harsh detergents.

Able to release stains associated with skin antibiotic creams and ointments.

Antibacterial efficacy against the survival of S. aureus, fungus, and molds on the fabric surface. Odors are prevented. Preferably, the fabric has an antimicrobial efficacy against E. Coli, Staph. Epidermidis, and P. Aeruginosa of at least about 99.4% per AATCC 100.

The data for the yarns of FIGS. 2 and 3 are compared with typical 55/45 polyester/cotton and 100% cotton bedding fabrics in Table I below.

TABLE I

|  | Units | FIG. 2 yarn | FIG. 3 yarn | Preferred Embodiment | Conventional Sheet | Conventional Sheet |
|---|---|---|---|---|---|---|
| Warp Yarn |  | 40/34 7z Nylon | 40/34 7z Nylon | 70/48 textured nylon | 55/45 Poly/cotton | 100% Cotton |
| Fill Yarn |  | 75/48 textured polyester | 70/72 textured nylon | 75/36 textured polyester | 55/45 Poly/cotton | 100% Cotton |
| Fabric Weight | osy | 2.53 | 2.51 | 2.43 | 3.72 | 3.44 |
| Yarns per Inch, machine direction | epi | 180 | 173 | 102 | 111 | 113 |
| Yarns per Inch, cross-machine direction | ppi | 110 | 107 | 104 | 79 | 84 |
| Avg. Elongation | % | 37.6 | 37.4 | 39.6 | 17.2 | 12.8 |
| Air Permeability | cfm/ft$^2$ | 10.7 | 9.2 | 30.5 | 39.5 | 39.4 |
| Circular Bend | N | 0.7 | 0.6 | 0.3 | 0.9 | 0.7 |
| Thermal Insulation Value | Clo | 0.49 | 0.50 | n/a | 0.53 | 0.55 |
| Soil Release to Oily Stains |  | 3.0 | 2.5 | 5.0 | 3.5 | 3.0 |
| Kinetic Coefficient of Friction (COF)-Warp direction |  | 0.53 | 0.35 | 0.22 | 1.10 | 1.00 |
| Kinetic COF-Fill |  | 0.50 | 0.56 | 0.23 | 1.08 | 1.03 |

TABLE I-continued

| | Units | FIG. 2 yarn | FIG. 3 yarn | Preferred Embodiment | Conventional Sheet | Conventional Sheet |
|---|---|---|---|---|---|---|
| Avg. Surface Roughness | μ | 1.4 | 1.1 | 1.5 | 3.7 | 2.3 |
| Fabric Dryness after 1 hour | % | 100% | 100% | 100% | 51% | 52% |

Certain modifications and improvements will occur to those skilled in the art upon a reading of the foregoing description. For example, the invention may be carried out with weaves other than plain weaves or twill weaves. The weaves of the invention create a smooth flat surface, without any three-dimensional surface structures that might unduly abrade skin. Other weaves that could be substituted include satin, sateen, or duck weaves. It should be understood that all such modifications and improvements have been deleted herein for the sake of conciseness and readability but are properly within the scope of the following claims.

What is claimed is:

1. A fabric comprising:
a woven fabric having warp yarns and filling yarns, wherein the warp yarns are about 30 denier to 100 denier, and the filling yarns are about 30 denier to 100 denier, wherein the warp yarns and filling yarns are woven together in a plain weave to provide a pill resistant fabric having identical surfaces on both sides thereof;
one of the warp or filling yarns being 100% continuous filament nylon making up at least 40% by weight of the fabric, wherein all of the filaments therein have round cross sections;
the other of the warp or filling yarns being continuous filament polyester or nylon making up the remainder of the weight of the fabric, wherein all of the filaments therein have non-round cross sections; and
wherein the woven fabric is finished such that the woven fabric has an elongation greater than about 30% as measured in accordance with ASTM D5034-95.

2. The fabric according to claim 1, wherein the warp yarns are 100% nylon.

3. The fabric according to claim 2, wherein the filling yarns are 100% polyester.

4. The fabric according to claim 1, wherein the filling yarns are 100% nylon.

5. The fabric according to claim 1, wherein an antimicrobial substance is topically applied or inherently available in the fabric.

6. The fabric according to claim 1, wherein the warp yarn is a 70 denier, 48 filament, textured, continuous filament nylon yarn.

7. The fabric according to claim 1, wherein the filling yarn is a 75 denier, 36 filament, continuous filament textured polyester.

8. The fabric according to claim 1, wherein the non-round filament cross sections are star shaped cross sections.

9. The fabric according to claim 1, wherein the non-round filament cross sections are clover leaf cross sections.

10. The fabric according to claim 1, wherein the continuous filament warp or filling yarns with non-round filament cross sections are configured such that adjacent filaments form wicking channels.

11. The fabric according to claim 1, further comprising a soil-release topical finish.

12. A fabric comprising:
a woven fabric having warp yarns and filling yarns woven together in a plain weave to provide a pill resistant fabric having identical surfaces in both sides thereof;
the warp yarns being 100% continuous filament 70 denier, 48 filament, textured nylon yarn making up at least 40% by weight of the fabric, wherein all of the filaments therein have round cross sections;
the filling yarns being up to about 60% by weight of the fabric of continuous filament 75 denier, 36 filament, textured polyester making up the remainder of the weight of the fabric, wherein all of the filaments therein have non-round filament cross sections that are star shaped or clover leaf shaped; and
wherein the woven fabric is finished such that the woven fabric has an elongation greater than about 30% as measured in accordance with ASTM D5034-95.

13. The fabric according to claim 12, further comprising a soil-release topical finish.

14. A fabric comprising:
a woven fabric having warp yarns and filling yarns woven together in a plain weave to provide a pill resistant fabric having identical surfaces on both sides thereof;
one of the warp or filling yarns being 100% continuous filament nylon making up at least 40% by weight of the fabric, wherein all of the filaments therein have round cross sections;
the other of the warp or filling yarns being continuous filament polyester or nylon and making up the remainder of the weight of the fabric, wherein all of the filaments therein have non-round cross sections; and
wherein the woven fabric is finished such that the woven fabric has an elongation greater than about 30% as measured in accordance with ASTM D5034-95.

15. The fabric according to claim 14, wherein the fabric has an average Kawabata geometric roughness of less than about 1.7 microns.

16. The fabric according to claim 14, wherein the fabric has a percent (%) dryness after 1 hour of 100%.

17. The fabric according to claim 14, wherein the fabric has an antimicrobial efficacy against *Escherichia coli, Staphylococcus epidermidis*, and *Pseudomonas aeruginosa* (per AATCC 100) of at least about 99.4%.

18. The fabric according to claim 12, further comprising an antimicrobial substance topically applied or inherently available in the fabric.

19. A fabric comprising:
a woven fabric having warp yarns and filling yarns, wherein the warp yarns are about 30 denier to 100 denier, and the filling yarns are about 30 denier to 100 denier, wherein the warp yarns and filling yarns are woven together in a plain weave to provide a pill resistant fabric having identical surfaces on both sides thereof;
one of the warp or filling yarns being 100% continuous filament nylon making up at least 40% by weight of the fabric, wherein all of the filaments therein have round cross sections;

the other of the warp or filling yarns being continuous filament polyester or nylon making up the remainder of the weight of the fabric, wherein all of the filaments therein have star shaped cross sections, and wherein the continuous filament warp or filling yarns with star shaped filament cross sections are configured such that adjacent filaments form wicking channels; and wherein the woven fabric is finished such that the woven fabric has an elongation greater than about 30% as measured in accordance with ASTM D5034-95.

20. The fabric according to claim 19, wherein the warp yarns are 100% nylon.

21. The fabric according to claim 20, wherein the filling yarns are 100% polyester.

22. The fabric according to claim 19, wherein the filling yarns are 100% nylon.

23. The fabric according to claim 19, wherein an antimicrobial substance is topically applied or inherently available in the fabric.

24. The fabric according to claim 19, wherein the warp yarn is a 70 denier, 48 filament, textured, continuous filament nylon yarn.

25. The fabric according to claim 19, wherein the filling yarn is a 75 denier, 36 filament, continuous filament textured polyester.

26. The fabric according to claim 19, further comprising a soil-release topical finish.

27. A fabric comprising:
a woven fabric having warp yarns and filling yarns, wherein the warp yarns are about 30 denier to 100 denier, and the filling yarns are about 30 denier to 100 denier, wherein the warp yarns and filling yarns are woven together in a plain weave to provide a pill resistant fabric having identical surfaces on both sides thereof;

one of the warp or filling yarns being 100% continuous filament nylon making up at least 40% by weight of the fabric, wherein all of the filaments therein have round cross sections;

the other of the warp or filling yarns being continuous filament polyester or nylon making up the remainder of the weight of the fabric, wherein all of the filaments therein have clover leaf shaped cross sections, and wherein the continuous filament warp or filling yarns with clover leaf shaped filament cross sections are configured such that adjacent filaments form wicking channels; and wherein the woven fabric is finished such that the woven fabric has an elongation greater than about 30% as measured in accordance with ASTM D5034-95.

28. The fabric according to claim 27, wherein the warp yarns are 100% nylon.

29. The fabric according to claim 28, wherein the filling yarns are 100% polyester.

30. The fabric according to claim 27, wherein the filling yarns are 100% nylon.

31. The fabric according to claim 27, wherein an antimicrobial substance is topically applied or inherently available in the fabric.

32. The fabric according to claim 27, wherein the warp yarn is a 70 denier, 48 filament, textured, continuous filament nylon yarn.

33. The fabric according to claim 27, wherein the filling yarn is a 75 denier, 36 filament, continuous filament textured polyester.

34. The fabric according to claim 27, further comprising a soil-release topical finish.

* * * * *